United States Patent [19]

Horiba et al.

[11] Patent Number: 4,769,757

[45] Date of Patent: Sep. 6, 1988

[54] IMPROVED CT SCANNER HAVING DISTORTION-FREE IMAGE

[75] Inventors: Isao Horiba, Aichi; Hiroyuki Takeuchi; Hiroshi Nishimura, both of Chiba, all of Japan

[73] Assignee: Hitachi Medical Corporation, Tokyo, Japan

[21] Appl. No.: 854,555

[22] Filed: Apr. 21, 1986

[30] Foreign Application Priority Data

May 22, 1985 [JP] Japan ................... 60-109764

[51] Int. Cl.$^4$ ............................................. G06F 15/42
[52] U.S. Cl. .................................. 364/413.19; 378/901
[58] Field of Search ...................... 364/414; 378/901; 250/363 S

[56] References Cited

U.S. PATENT DOCUMENTS

| Re. 30,947 | 5/1982 | Boyd | 364/414 |
|---|---|---|---|
| 4,266,136 | 5/1981 | Duinker | 364/414 |
| 4,570,224 | 2/1986 | Shimoni et al. | 378/901 |
| 4,682,291 | 7/1987 | Reuveni | 364/414 |

Primary Examiner—Jerry Smith
Assistant Examiner—Kimthanh Tbui
Attorney, Agent, or Firm—Gerald J. Ferguson, Jr.

[57] ABSTRACT

A CT scanner including a scanning device including (a) device for rotating an x-ray source around an object to be examined, the x-ray source radiating x-rays, while the x-ray source is being rotated, in the form of fan beams covering a region of the object to be examined, and (b) a multielement x-ray detector for detecting x-ray fan beams transmitted through the object to thus collect data around the irradiated object; an arithmetic device for arithmetically reconstructing the distribution of the x-ray absorption coefficients of the object across a measured cross-section from the data; and a display for displaying the distribution where the arithmetic device includes a device for producing data equivalent to data derived from parallel beams not regularly spaced apart from each other from the collected data around the irradiated object, a device for subjecting the produced data to filtering, and a device for correcting inhomogeneity in the data equivalent to data derived from parallel beams not regularly spaced and for back-projecting the image of the distribution.

3 Claims, 7 Drawing Sheets

IMPROVED CT SCANNER HAVING DISTORTION-FREE IMAGE

BACKGROUND OF THE INVENTION

1. Technical Field of the Invention

The present invention relates to a CT scanner which examines an object using x-rays in the form of a fan beam while rotating around the object and, more particularly, to a CT scanner which is able to produce high-quality tomograms and rapidly perform arithmetic operations needed to reconstruct images.

2. Description of the Prior Art

FIG. 8 shows the structure of a conventional CT scanner of this kind and a method of measurement. An x-ray source S emits x-rays 2 in the form of a fan beam which covers the region 1 of an object 4 to be examined. A multielement x-ray detector 3 is disposed opposite to the source S. The source S rotates around the object 4 to be examined, together with the detector 3. During this rotation, pulsive x-rays are radiated to the object 4 and pass through it. The transmitted fan beam is detected at an angular interval in the source and the detector rotation by detecting elements 3' that are regularly spaced apart from each other in the detector 3 whenever the source and the detector rotate through a discrete step angle. The data about the irradiated object is collected. Assume neighboring elements 3' of the detector 3 are spaced an angle of $P_\alpha$ from each other and that the x-ray source and the detector rotate a discrete step angle of $P_\beta$ for measurement. The obtained data is given by H ($\alpha$, $\beta$), where $\beta$ is the angular position of the x-ray source and $\alpha$ indicates the angular position of each detecting element within the array. The data can be obtained by integrating the x-ray absorption coefficient distribution f (x, y) of the object 4 along the detected x-ray fan beam l (x, y). That is, $$H(\alpha,\beta) = \int f(x, y)dl \quad (1)$$

Filtered back projection is the well-known method of reconstructing a tomogram f (x, y) from the data H ($\alpha$, $\beta$) obtained in this way. For example, see "The Fourier Reconstruction of a Head Section", 1974, IEEE TRans., NS-21 pp. 21–43. Referring to FIG. 9, this filtered back projection comprises the steps of acquiring data (A) by projection of x-rays onto an object to be examined, variously prepocessing the data (B) for correcting the physical characteristics of the detector, then subjecting the data to filtering (C) for correcting blur owing to back projection, and subsequently performing arithmetic operations (D) for back projection to reconstruct a tomogram.

In acquiring the data about the transmitted x-ray through the object as described above, the relation between the corrdinate space used for the arithmetic reconstruction operation and the geometry for detection is represented as shown in FIG. 10 using a cartesian coordinate space. In this figure, the position of an x-ray source S is given by angle $\beta$. The position of a beam passing through a picture element E (x, y) within a fan beam radiated from the position S is given by the angle $\alpha$ that the beam makes with the straight line passing through the center of rotation O from the position S. Let L be the distance between x-ray source S and the picture element E (x, y). The radius of the circule drawn by the source S is indicated by D.

As described above, the data obtained from various directions is subjected to filtering (C) (see FIG. 9) and then the data is arithmetically processed (D) so that the data is directly back-projected in a fan-shaped manner onto a two-dimensional memory space constructed as a cartesian coordinate space. This method is known as direct back projection. According to this method, as described in, for example, U.S. Pat. No. 4,149,247, the data H ($\alpha$, $\beta$) obtained by projected fan beams first undergoes a filtering as given by $$G(\alpha, \beta) = \int J(\alpha')W(\alpha')H(\alpha-\alpha', \beta)d\alpha' \quad (2)$$

where J ($\alpha'$) is a term for correcting for the nonuniform intervals between detecting elements and is approximately given by $$J(\alpha') = \cos(\alpha') \quad (3)$$

and W is a filter function for removing blur. Then these filtered data are back-projected later. More specifically, referring still to FIG. 10, the position of the x-ray source S and the coordinate E (x, y) that is arithmetically processed for reconstruction are given. The angle $\alpha$ that the x-ray beam passing through the point E makes is calculated according to the following equations (4) and (5).

$$\alpha = -\beta + \gamma \quad (4)$$

$$\gamma = \tan^{-1}\left(\frac{y - D \sin \beta}{y - D \cos \beta}\right) \quad (5)$$

Then, weight L is calculated according to the following equation.

$$L^2 = (x - D \cos \beta)^2 + (y - D \sin \beta)^2 \quad (6)$$

Using G and $L^2$, data about all the coordinates are summed up from the initial position at which $\beta = 0°$ to the final position at which $\beta = 360°$ according to equation (7) to reconstruct a tomogram.

$$f(x, y) = \int_{\beta=\beta_0}^{\beta_0+2\pi} \frac{1}{L^2} G(\alpha,\beta)d\beta \quad (7)$$

where $1/L^2$ is a weight for correcting a partial fan-beam effect that the x-ray beam directed from the x-ray source S toward the detector 3 experiences.

The two sets of data H ($\alpha$, $\beta$) derived by measurement are quantized at intervals of $P_\alpha$ and $P_\beta$, respectively. Using integers j and m, $\beta$ is rewritten as $$\beta = \beta_0 + P_\beta \times j = \beta(j) \quad (j=0, 1, 2, \ldots, m-1) \quad (8)$$

$$m = 2\pi/P_\beta \quad (9)$$

where $\beta_0$ is the initial position of the measurement and j indicates the number given to a projected fan beam. Since j is discretized, equation (7) is modified as $$f(x, y) = P_\beta \sum_{j=0}^{m-1} \frac{1}{L^2} G(\alpha, \beta(j)) \qquad (10)$$

With respect to $\alpha$, the values of a $\alpha$ found based on the coordinate (x, y) according to equations (4) and (5) do not always coincide with the measuring points. Therefore, instead of using equation (10), it is the common practice to calculate values according to equation (11), making use of linear interpolation taken at four close points.

$$f(x, y) = P_\beta P_\alpha \sum_{j=0}^{m-1} \frac{1}{L^2} \sum_{n=-1}^{2} gn(\delta)G\{\alpha(i + n), \beta(j)\} \qquad (11)$$

where gn ($\delta$) is an interpolation function, and i and $\delta$ are given by $$i = [\alpha/p\alpha] \qquad (12)$$

$$\delta = \alpha - P\alpha X i \qquad (13)$$

where [ ] is the Gausian symbol.

By performing these prcessings about every coordinate, the arithmetic operations for back projection are completed. For this purpose, the calculations according to equations (4), (5), (6), and (11) must be repeated many times equal to the number of all the picture elements multiplied by the number of projected beams, i.e., the number of incremental steps. Accordingly, the direct back projection needs an exorbitant amount of calculation. The amount increases further as intervals between the detecting elements are narrowed and the number of picture elements of a tomogram is increased to improve the quality of image. This hinders rapid calculation for reconstructing the image.

U.S. Pat. No. Re. 30947 disclosed another method, known as the re-ordering and re-bining method, in which data items obtained by projection of x-ray fan beams are rearranged to create data equivalent to data obtained by using parallel beams. The resultant data are subjected to filtering (C), and arithmetic operations (D) for back projection are performed (see FIG. 9). Referring back to FIG. 8, the multielement x-ray detector 3 has elements which are regularly and circumferentially spaced P from each other about the x-ray source S. Data H ($\alpha$, $\beta$) is obtained by the detector 3 from the projected fan beams. The re-ordering and re-bining method is now described in detail by referring to FIG. 11, where a two-dimensional coordinate space (see FIG. 12) having two parameters is set. One of the parameters is the distance t between the center of rotation O of both the detector 3 and the x-ray source S and each x-ray beam, the other parameter being the angle $\theta$ that each beam makes. The angle $\alpha$ and $\beta$ and the axis t and $\theta$ of the two-dimensional coordinate space are interrelated by $$t = D \times \sin \alpha \qquad (14)$$

$$\theta = \alpha + \beta \qquad (15)$$

Therefore, the angular intervals P$\alpha$ between the detecting elements in the direction of the t axis of the two-dimensional coordinate space are reduced as the distance t increases. The data items about the projected object are arranged into S-shaped form on the two-dimensional coordinate space according to the angular position $\beta$ of the x-ray source, as shown in FIG. 12. The data P (t, $\theta$) on the two-dimensional coordinate space are derived from projected parallel beams. After the arithmetic operations, the data P (t, $\theta$) are arithmetically processed for back projection so that they correspond to parallel beams, whereby a tomogram is reconstructed. In the case of FIG. 12. the ratio K of the angular intervals P$\alpha$ between the detecting elements to the incremental steps P$\beta$ for measurement is equal to $\frac{1}{2}$.

However, the re-ordering and re-bining method has a disadvantage in that the data drawn on the two-dimensional coordinate space is given by a curve as shown in FIG. 12. Further, since the detecting positions of the detecting elements are not regularly spaced apart, this conversion to the two-dimensional coordinate space is unable to make the lattice points and the measuring points agree with all data items. In general, one-dimensional interpolation is effected along the direction of $\beta$, and then other one-dimensional interpolation is carried out to correct inhomogeneity in the direction of $\alpha$. Or, these two interpolations are combined to perform two-dimensional interpolation in the directions of $\alpha$ and $\beta$. Thus, the reordering and re-bining method suffers from a improvement in the spatial resolution of the reconstructed tomogram because of the two one-dimensional interpolations or the two-dimensional interpolation. Further, the tomogram contains coarser noise components, thus deteriorating the quality of image.

OBJECT OF THE INVENTION

Accordingly, it is the object of the present invention to provide a CT (computerized tomography) scanner which is free of the foregoing problems, is capable of producing tomograms of improved quality, and is able to rapidly perform arithmetic operations needed to reconstruct images. This and other objects of the invention will become apparent from a reading of the following specification and claims, taken with the drawing.

DETAILED DESCRIPTION OF PREFERRED EMBODIMENTS OF THE INVENTIONS

Figure 1:
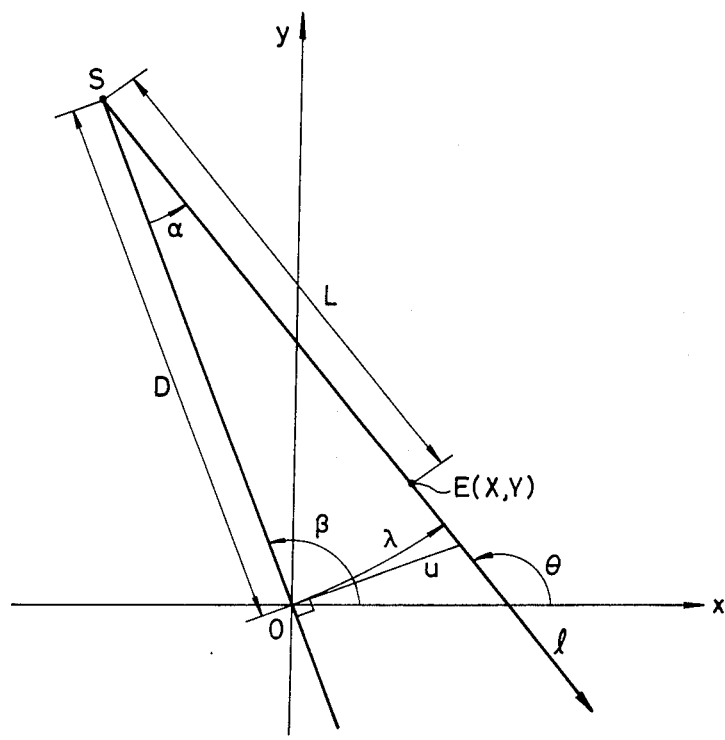
FIG. 1 shows the relation between a coordinate space for arithmetic operations for reconstruction and the geometry for measurement in acquiring data resulting from projection of x-rays by a CT scanner according to the invention, the coordinate space and the geometry being shown on a Cartesian coordinate space.

FIG. 1 shows the relation between the coordinate space for arithmetic operations for reconstruction and the geometry for measurement in a Cartesian coordinate system in acquiring data about an projected object, using a CT scanner according to the invention, the scanner not suffering from deterioration in quality of image, unlike the prior art instrument. In this figure, the position of an x-ray source S is indicated by angle $\beta$. The position of the beam which is radiated from the position S and passes through a picture element E (x, y) lying within the fan beam with respect to the straight line passing through the center of rotation O from the position S is indicated by angle $\alpha$. Let L be the distance between the source S and the picture element E (x, y). The x-ray source S rotates while drawing a circle having a radius of D. The distance between the center of rotation O of the x-ray source S and each x-ray beam as measured along the normal to the straight line SO is defined as U. The angle that each x-ray beam makes is defined as $\theta$.

Figure 2:
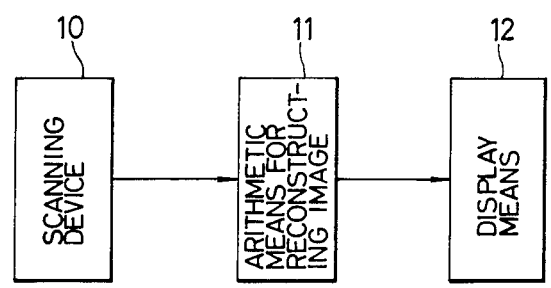
FIG. 2 is a block diagram showing the whole structure of an illustrative CT scanner.
Figure 11:
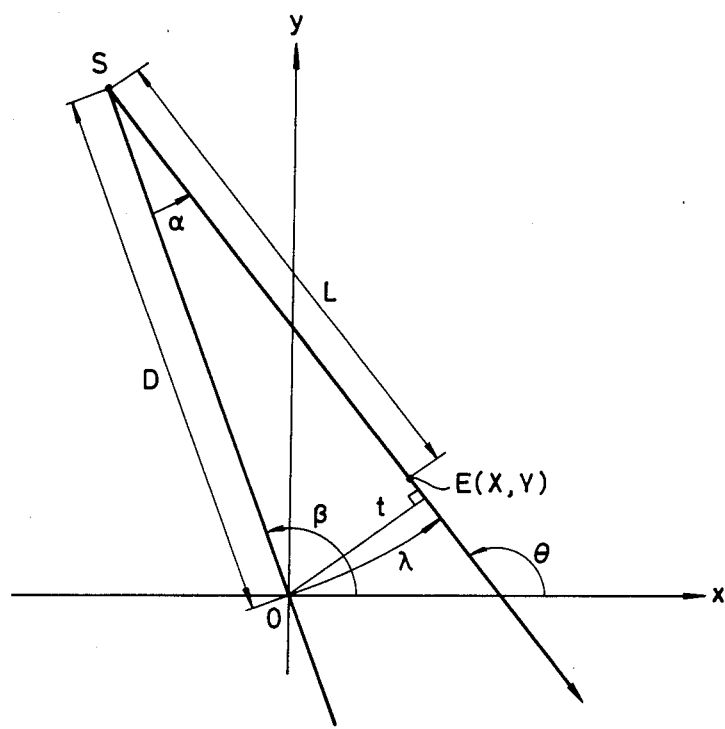
FIG. 11 is a view similar to FIG. 10, but showing the conventional reordering and re-binding method.

Referring to FIG. 2, the invention employs a scanning device 10, an arithmetic means 11 for reconstructing image, and a display means 12. The arithmetic means 11 comprises a data-producing means, a filtering means, and a correcting-and-back projecting means. The data-producing means newly introduces a modified two-dimensional coordinate space which uses the length u instead of the aforementioned coordinate axis t (FIG. 11). This length u differs from the actually measured value but is proportion to the inverse sine of t/D as given by equation (16) below. The data-producing means further acts to perform arithmetic operations for rearranging data items on the two-dimensional coordinate space to produce data equivalent to data derived from parallel beams not regularly spaced apart from each other. The produced data are subjected to filtering process by the filtering means. The correcting-and-back projecting means corrects the inhomogeneity in the data and back-projects the distribution image.

$$u = \sin^{-1}(t/D) = \alpha \qquad (16)$$

$$\theta = \alpha + \beta$$

Figure 3:
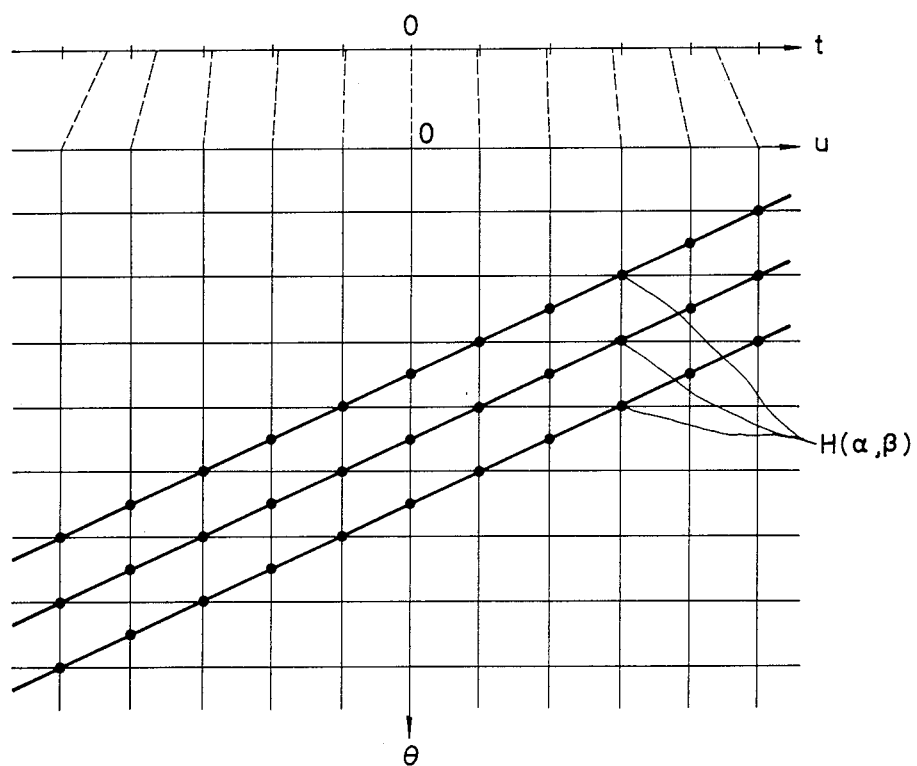
FIG. 3 is a graph showing positions at which detection is made, on a two-dimensional coordinate space introduced by the invention.

The detecting positions on the modified two-dimensional coordinate space are shown in FIG. 3, and in this coordinate space the newly introduced distance u between the center of rotation O and each x-ray beam and the angle $\theta$ that each beam makes are taken as parameters. In the case of FIG. 3, the ratio K of the angular intervals $P_\alpha$ between the detecting elements to the incremental steps $P_\beta$ between the detecting elements to the incremental steps $P_\beta$ for measurement is equal to $\frac{1}{2}$.

Figure 12:
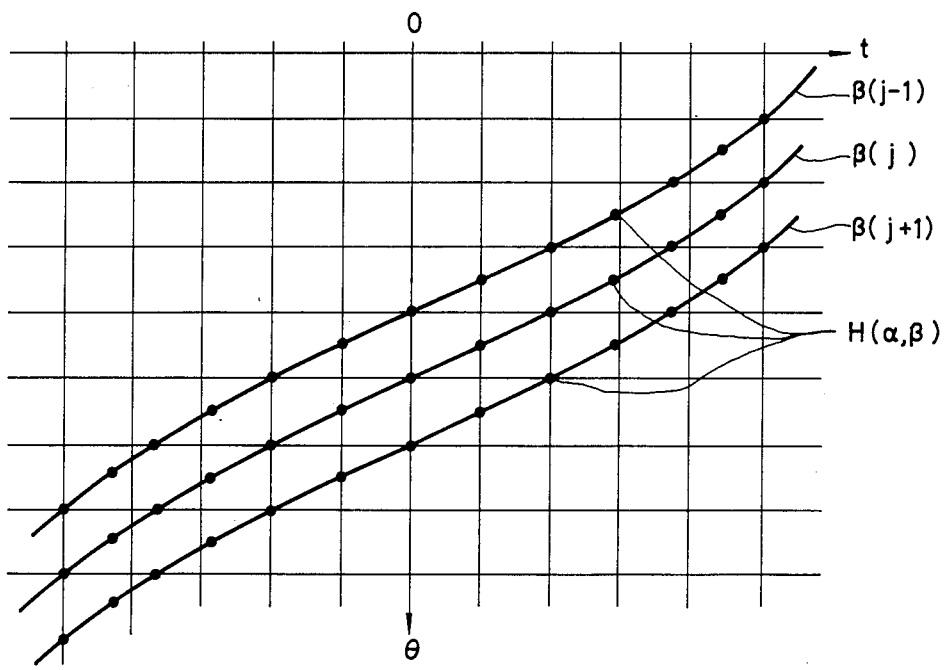
FIG. 12 is a graph showing detecting positions on the two-dimensional coordinate space used in the re-ordering and re-binding method.

The resultant data P (u, $\theta$) represented on the modified two-dimensional coordinate space differs from the data P (t, $\theta$) represented on the conventional two-dimensional coordinate space shown in FIG. 12, because the coordinate axis u differs from the actually measured value. The interval Pu in the direction of u gradually decreases as the distance from the center of rotation O of both the x-ray source S and the detector 3 increases. This phenomenon will hereinafter be referred as inhomogeneity in u. If the data were directly arithmetically processed for ordinary parallel beams to reconstruct a tomogram, the tomogram would be gradually enlarged radially, i.e., from the center of rotation O toward the peripheral portions. Further, the absorption coefficients of x-rays would not be correctly found. These problems are solved by filtering and arithmetic operations for back projection are corrected by filtering. The enlarging effect at the peripheral portions is compensated for by arithmetic operations for back projection.

The correction of the absorption coefficients of x-rays is first described. In the filtering process, a function for stressing the frequency substantially in proportion to spatial frequency is used to correct blur caused by black projection that will be effected later. From equation (16), we have $$dt = D \cos(u) \cdot du \qquad (18)$$

Therefore, the values obtained after the data is subjected to filtering using the coordinate axis u having nonlinear relation to the actually measured value t is modulated by an amount proportional to the cosine of the inhomogenous component u and so the value after filtering becomes smaller toward the peripheral portions. In order to correct for this, the data P (u, $\theta$) is subjected to filtering by the use of a filter function W as given by $$G(u,) = \int J(u) W(u') P(u - u',) du' \qquad (19)$$

where J (u) is a term for correcting the inhomogeneity in the coordinate axis u and is given by $$J(u) = 1/\cos(u) \tag{20}$$

The filtering expressed by equation (19) takes the form of superimposed integrals. Mathematically, exactly the same calculation can be performed by the use of Fourier transformation.

The enlarging effect at the peripheral portions that occurs in performing arithmetic operations for back projection is compensated for in the manner described below. The data obtained from ordinary parallel beams regularly spaced apart from each other are given by P $(t,\theta)$. The data is processed for back projection as follows:

$$t = X \sin\theta - y \cos\theta \tag{21}$$

$$f(x, y) = \int_{\theta=0}^{2\pi} P(t, \theta) \, d\theta \tag{22}$$

The data G $(u, \theta)$ found according to equation (19) is used as data P $(t, \theta)$ derived using ordinary parallel beams regularly spaced. The data is then back-projected according to equation (22) to reconstruct image f $(x, y)$. This image is modulated by an amount proportional to the inverse sine of t/D because of the inhomogeneity in the coordinate axis u. As a result, the image is stressed toward the peripheral portions. For this reason, an amendment is made to equation (21). That is, using $$u = \sin^{-1}(t/D) = \sin^{-1}\{(x\sin\theta - y\cos\theta)/D\} \tag{23}$$

the values of u are found from the coordinates (x, y) of the reconstructed image. The reconstructed image f (x, y) is derived according to equation (24).

$$f(x, y) = \int_{\theta=0}^{2\pi} G(u, \theta) \, d\theta \tag{24}$$

It is to be noted that the two sets of filtered data G (u, $\theta$) are quantized at intervals of Pu and P$\theta$, respectively. Therefore, in the same manner as in the direct back projection, is expressed using integers j and m as follows:

$$\theta = \theta_0 + P^\theta X j = \theta(j) \quad (j = 0, 1, 2, \ldots, m-1) \tag{25}$$

$$m = 2\pi/P^\theta \tag{26}$$

where $\theta_0$ is given by $$\theta_0 = \alpha_0 + \beta_0 \tag{27}$$

where $\alpha_0$ half of the angle of spread of a fan beam and $\beta_0$ is the initial position of a measurement. In order to discretize the integer j, equation (24) is put into the form $$f(x, y) = p\theta \sum_{j=0}^{m-1} G\{u, \theta(j)\} \tag{28}$$

Also, the values of u derived from the coordinates (x, y) which have been quantized according to equation (23) do not always agree with the values obtained from G (u, j). Therefore, linear interpolation at four close points is used instead of equation (28), and equation (29) is employed for calculation.

$$f(x, y) = P\theta Pu \sum_{j=0}^{m-1} \sum_{n=-1}^{2} gn(\delta) \, G\{u(i + n), \theta(j)\} \tag{29}$$

where gn ($\delta$) is an interpolation function, and i and $\delta$ are given by $$i = [u/Pu] \tag{30}$$

$$\delta = u - Pu \times i \tag{31}$$

where [ ] is a Gausian symbol.

When the modified two-dimensional coordinates (u, $\theta$) according to the invention are used, the coordinate axis u exactly agrees with the measured position $\alpha$, thus dispensing with calculation for interporation in the direction of $\beta$ that determines the spatial resolution. The data items obtained from an irradiated object are arranged linearly on the modified two-dimensional coordinate space according to the angular position $\beta$ of the x-ray source S. This greatly simplifies the calculation for interpolation in the direction of $\beta$. In general, CT scanners using x-rays in the form of a fan beam often set the angular intervals P$\beta$ between the detecting elements so as to be less than the incremental steps P. In this case, the data items on the modified two-dimensional coordinate space are arranged on straight lines whose inclination to the axis u is less than 1. The rearrangement needed to obtain data equivalent to data obtained using parallel beams can be executed by a simple one-dimensional interpolation calculation in the direction of $\beta$.

When the scanning device 10 is so designed that x-ray source S radiates x-rays whenever it moves a discrete angle which is an integer times as large as the angular intervals P$_\alpha$ between the regularly spaced detecting elements of the multielement x-ray detector, i.e., when the incremental steps P$\beta$ are so set as to be an integer K times as large as the angular intervals P$_\alpha$ between the detecting elements (P = KP ), calculations for interpolation can be realized by simply repeating a calculation with period K. This further simplifies the arithmetic operations for rearrangement. For example, when the angular intervals P between the detecting elements are equal to the incremental steps P, i.e., K=1, the intervals PQ between the lattices of the coordinate axis are made to coincide with P. Thus, the data items on the modified two-dimensional coordinate space are arranged on straight lines having an inclination of 1 to the axis u. The positions of the detecting elements coincide with the lattice points on the two-dimensional coordinate space for all data items. Consequently, calculation for interpolation is rendered completely unnecessary.

One illustrative embodiment of the invention is hereinafter described in detail with reference to the accompanying drawings.

FIG. 2 is a block diagram of the whole structure of a CT scanner according to the present invention. This CT scanner consists of three components—a scanning device 10 for making measurement, an arithmetic means 11 for reconstructing a tomogram from the data obtained by the scanning device 10, and a display means 12 for displaying the tomogram.

Figure 4:
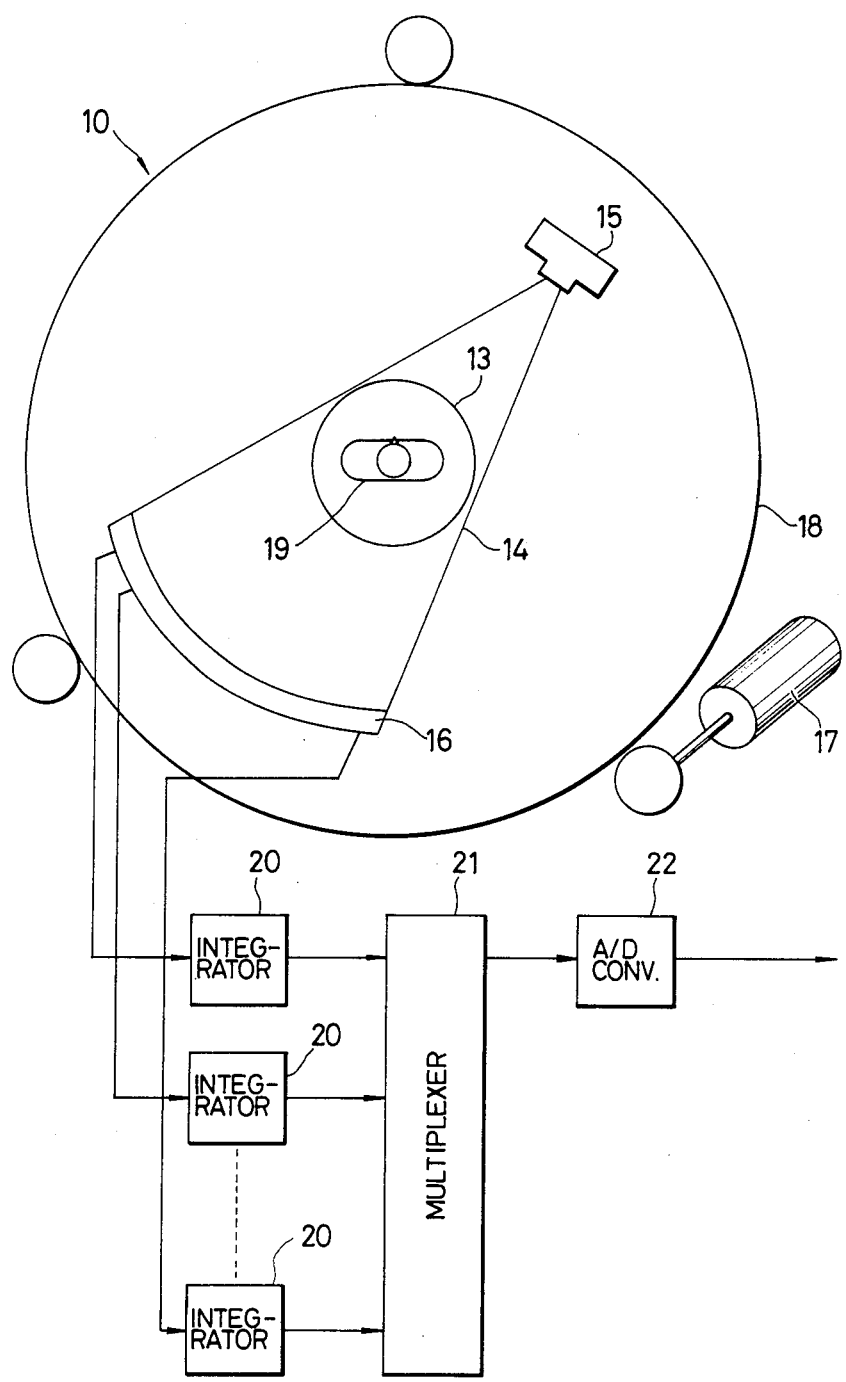
FIG. 4 is a block diagram showing illustrative structure of a scanning device.

Referring next to FIG. 4, the structure of the scanning device 10 is shown. The scanning device 10 has a rotatable disk 18 driven by a driver device 17. Mounted on the disk 18 are an x-ray tube 15 and a multielement x-ray detector 16 disposed opposite to the tube 15. The x-ray tube 15 produces x-rays 14 in the form of a fan beam that covers the region 13 of an object 19 to be examined. These make a rotary motion around the object 19 to be examined as a unit. Each time the disk and the components move a discrete step angle, pulsive x-rays are radiated toward the object 19. The intensity of the transmitted x-rays is detected by the multielement detector 16 in which detecting elements are regularly spaced apart from each other. The electrical signals produced by the elements of detector 16 are integrated during the pulse width of the x-rays by integrator circuits 20. The output signals from integrator circuits 20 are applied via an analog multiplexer 21 to an analog-to-digital converter 22, where the signal is converted to digital form. In this way, the scanning device 10 makes a full revolution, i.e., rotates through 360°, and all the data collected during this period is applied to the following arithmetic image reconstruction means 11.

Figures 5, 6:
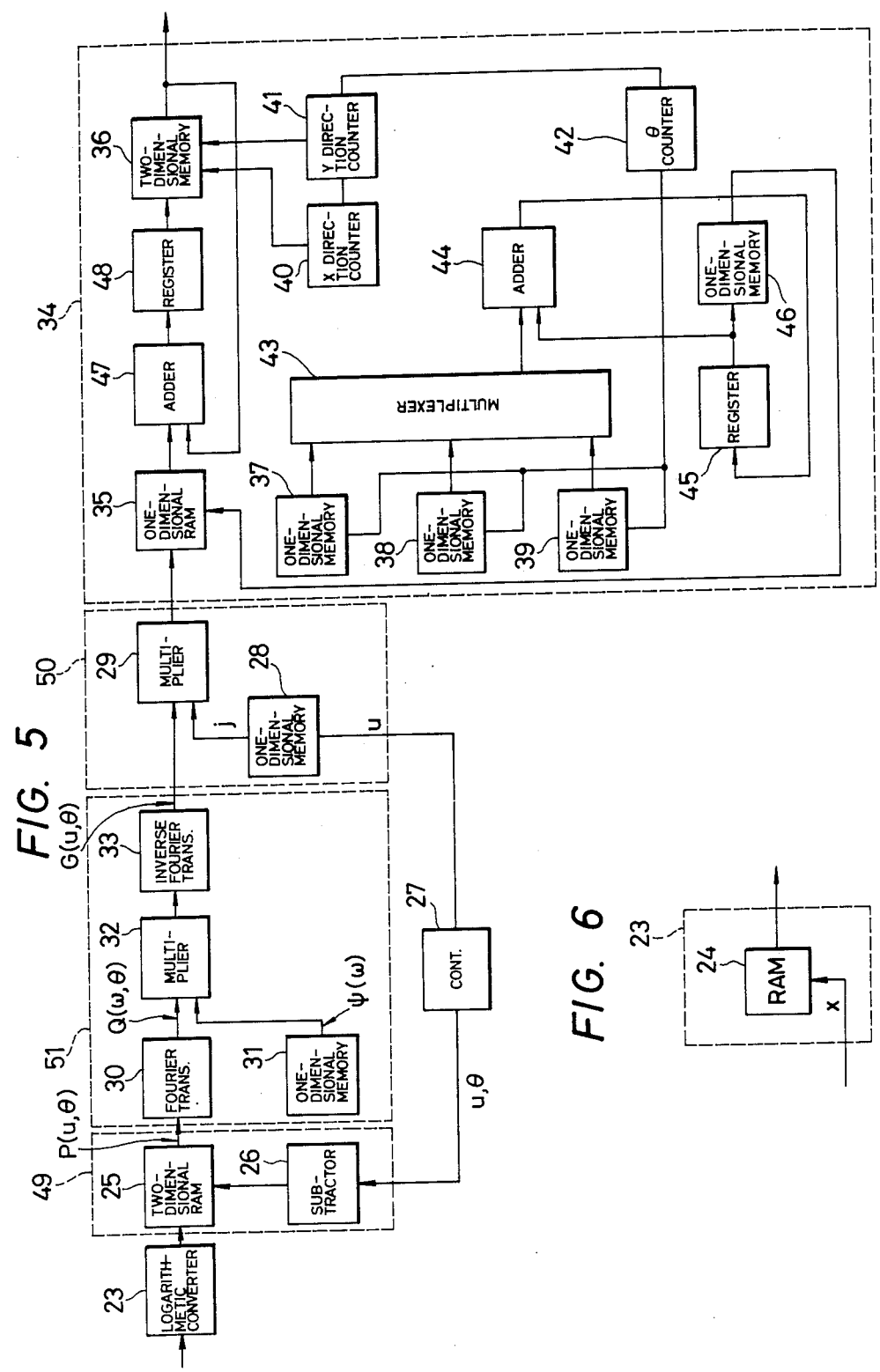
FIG. 5 is a block diagram illustratively showing a means for arithmetically reconstructing an image.
FIG. 6 is a block diagram showing illustrative contents of a logarithmic converter in FIG. 5.

Referring next to FIG. 5, an illustrative structure of the arithmetic means 11 for reconstructing image is shown. The data applied to the arithmetic means 11 are converted by a logarithmic converter 23 into integrated values H ($\alpha$, $\beta$), as indicated by equation (1), having x-ray absorption coefficient distribution f (x, y) that the object 19 exhibits along l (x, y) of the fan beam. This logarithmic converter 23 can be formed by a simple random access memory 24 as shown in FIG. 6. A table of logarithmic function log (x) has been previously stored in the memory 24. A measured value x is applied to the address line of the momory 24 to obtain an output which is a logarithmic value of the input signal. The resultant data H ($\alpha$, $\beta$) is stored in a two-dimensional random access memory 25 shown in FIG. 5. The individual cells of the memory 25 are identified by $\alpha$ and $\beta$. A subtractor 26 performs the following operations.

$$\alpha = u \quad (32)$$

$$\beta = \theta - u \quad (33)$$

according to equations (18) and (19) whose U and $\theta$ are specified by a controller 27 to calculate the values of $\alpha$ and $\beta$. The values of $\alpha$ and $\beta$ are applied to the address line of the two-dimensional RAM 25, whereby data P (u, $\theta$) equivalent to data obtained using parallel beams is obtained from the data H ($\alpha$, $\beta$) derived using fan beams. The RAM 25 and the subtracter 26 constitute a means 49 for performing calculations for rearrangement on the modified two-dimensional coordinate space to produce data equivalent to data obtained using parallel beams not regularly spaced apart from each other. The Fourier transformer 30 transforms the axis u into spatial frequency $\omega$, resulting in Q ($\omega$, $\theta$). The Fourier transform $\psi$ ($\omega$) of a filter function W (u) for correcting for blur due to back projection is stored in a one-dimensional memory 31. A multiplier 32 produces an output that is the product of Q ($\omega$, $\theta$) and $\psi(\omega)$, and the output is supplied to an inverse Fourier transformer 33. The Fourier transformer 30, the one-dimensional memory 31, the multiplier 32, and the inverse Fourier transformer 33 constitute a means 51 for performing filtering processing.

Values of J in equation (22) are stored in a one-dimensional memory 28. The values of u specified by the controller 27 are applied to the address line of the memory 28 to produce the values of J, i.e. cos (u). A multiplier 29 produces an output that is the product of J and filtered P (u, $\theta$), the output being applied to the following arithmetic unit for back projection 34. The one-dimensional memory 28 and the multiplier 29 constitute a means 50 for correcting x-ray absorption coefficients. This means 50 is one of the means for correcting for errors in the data P (u, $\theta$) that was caused by the unequal distances from the center of rotation O. The data G (u, $\theta$) obtained by the filtering and correcting are once stored in a one-dimensional random access memory 35 in the following arithmetic unit 34 for back projection.

The arithmetic unit 34 performs arithmetic operations to produce a tomogram from the data G (u, $\theta$) obtained by filtering. This tomogram is reconstructed on a two-dimensional memory 36, which sums up the values of G (u, $\theta$) found for individual values of $\theta$ according to equation (29). This operation is performed for every coordinate along the x and y axes like raster scanning. That is, $\theta$ is varied from 0° to 360°. After completing all the summing operations, a tomogram is arithmetically created.

Figure 7:
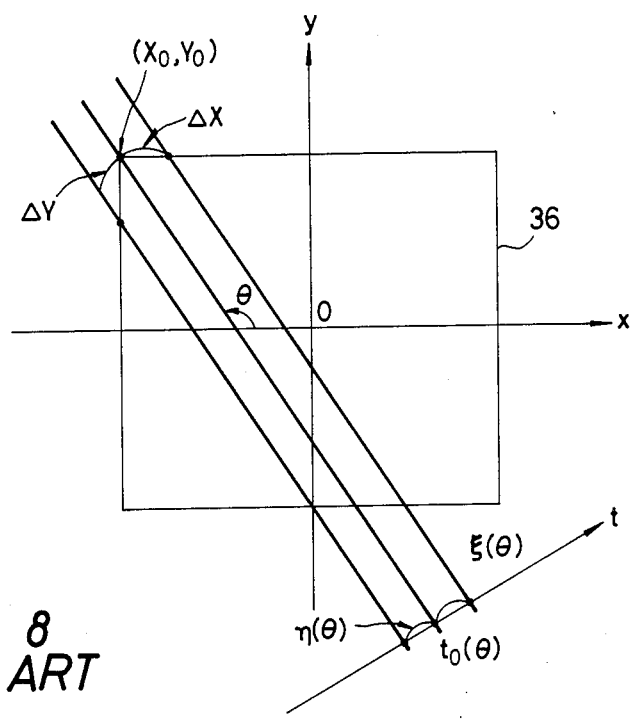
FIG. 7 shows the manner in which an arithmetic operation for back projection is performed for parallel x-ray beams.
Figure 8:
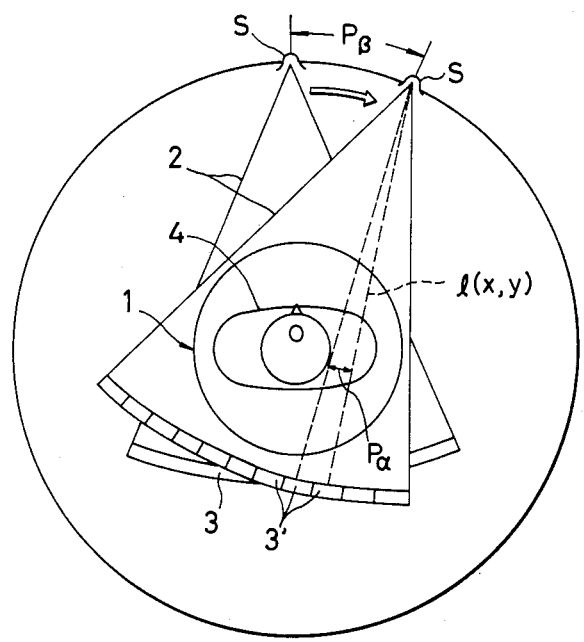
FIG. 8 shows the structure of a scanning device incorporated in a prior art CT scanner, as well as a method of measurement.
Figure 9:
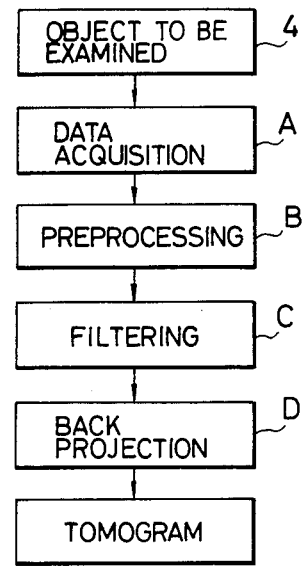
FIG. 9 shows the procedures of the filtered back projection method for reconstructing a tomogram.
Figure 10:
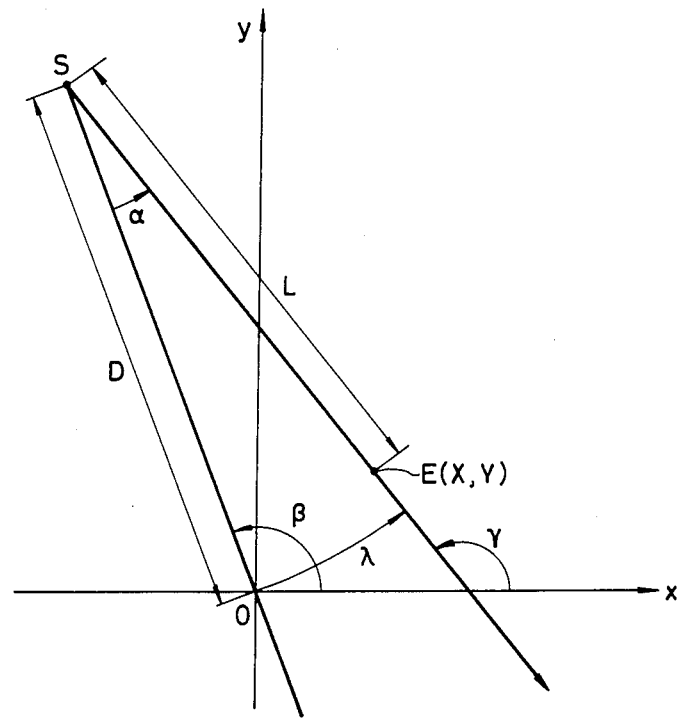
FIG. 10 shows the conventional relation between a coordinate space for calculation for reconstruction and the geometry for measurement on a Cartesian coordinate space in acquiring data resulting from projection of x-rays.

For a certain value of , a back projection is arithmetically found as illustrated in FIG. 7, where the coordinate at the top left point of the two-dimensional memory 36 is the starting point of the accumulation operation using equation (16). The position $t_0(\theta)$ of a parallel beam that passes through the coordinate $(x_0, y_0)$ is given by $$t_0(\theta) = x_0 \sin \theta - Y_0 \cos \theta \quad (34)$$

Displacement elements $\xi$ ($\theta$) and $\eta$ ($\theta$) on the axis t in the directions x and y axes, respectively, which result from the raster scanning on the two-dimensional memory 36 are given by $$\xi(\theta) = \Delta x \sin \theta \quad (35)$$

$$\eta(\theta) = -\Delta x \cos \theta \quad (36)$$

where $\Delta x$ and $\Delta y$ are intervals between the coordinates in the directions of x and y axes, respectively, on the memory 36. Accordingly, the displacement in the direction of the x axis caused by the raster scanning on the memory 36 can be found by increasing the position t of the parallel beams by $\xi$. Similarly, the displacement in the direction of the Y axis can be found by increasing it by $\eta$. Thus, the positions t of parallel beams passing through all the coordinates on the memory can be found by simple additive operations. The values of u can be easily found from the values of t using equation (23) and referring to a numerical table of sin (t/D).

Referring to FIG. 5, $t_0$, $\xi$, and $\eta$ are stored in one-dimensional memories 37, 38, 39, respectively. An x-direction counter 40 and a y-direction counter 41 are connected to the address lines of a two-dimensional memory 36. When processings for one raster scanning are completed, the counter 40 overflows, while the counter 41 is incremented. When the processings for all the raster scannings are completed, the y-direction counter 41 overflows, while a counter 42 for $\theta$ is incremented, and then the next value of $\theta$ is specified. The output from the counter 42 is coupled to the three one-dimensional memories 37–39 to read out $t_0$, $\xi$, $\eta$, respectively. The outputs of the memories 37–39 are connected to an adder 44 via a multiplexer 43. After a register 45 has been cleared, $t_0$ is applied to the register to initialize this register 45. While successive movements are made in the direction of x axis during the raster scanning, the adder 44 and the register 45 add up the values of $\xi$. While movements in the direction of y axis are made, they add up the values of $\eta$. Thus, the position t of the parallel beam corresponding to the coordinate (x, y) is found. A numerical table of sin (t/D) is stored in a one-dimensional memory 46. The output of the register 45 is connected to the address line of the memory 46 so that the position t is immediately converted to u. Among the means for correcting the unequal distances from the center of rotation O about the data P (u, $\theta$) corresponding to parallel beams, the memory 46 constitutes a means for correcting the peripheral portion-enlarging effect. Then, the obtained values of u are applied to the address line of the one-dimensional RAM 35 so that the data G (u, $\theta$) derived by filtering is read out. The data is added to the output from the two-dimensional memory 36 which is read by the x- and y-direction counters 40 and 41, by means of the adder 47 and the register 48. Then, the data is again stored in the memory 36.

After additive operations for all the coordinates on the two-dimensional memory 36 are performed described thus far for one value of $\theta$, thus completing arithmetic operations for back projection, the next value of $\theta$ is subjected to filtering, resulting in G (u, $\theta$). Then, similar operations are repeated. In this way, additive operations are performed for all the values of $\theta$, i.e., from 0° to 360° to arithmetically find a tomogram.

The tomogram obtained in this way is displayed on the following display means 12 (see FIG. 2). More specifically, the tomogram reconstructed on the two-dimensional memory 36 is successively read out as digital form like raster scanning. The digital data is then converted into video signal by the D/A converter. The video signal is applied to a cathode-ray tube, on which x-ray absorption coefficients are displayed as an image in gradations.

In the above example, the x-ray tube 15 rotates with the multielement detector 16. The invention is also applicable to an instrument in which the multielement detector 16 is arranged on, and fixed to, a circle so that only the x-ray tube 15 is rotated. In this instrument, the function representing coordinates not regularly spaced apart from each other is modified.

ADVANTAGES OF THE INVENTION

Since the invention is constructed as described above, the effect of the coordinate axis u differing from the actually measured values is completely compensated for, the axis u being set during the processings. Thus, the obtained tomogram is free of distortion and hence correct. Also, the invention does not use calculations for two-dimensional interpolation which have been required by the conventional re-ordering and re-binding method. Further, the calculation for interplation in the direction of $\alpha$ which causes deterioration in the spatial resultion of the reconstructed tomogram is only once for each projection, in the same manner as in the direct back projection. Therefore, the spatial resolution deteriorates only slightly. In addition, the coarseness of noise is mitigated. Furthermore, the invention can omit equations (5) and (6) which were used by the direct back projection and required a long time for calculation. Hence, the tomogram can be arithmetically reconstructed much more rapidly than conventional. Yet further, the filtering and calculations for back projection have strong resemblance to a CT scanner using parallel beams and so the novel CT scanner has a great deal in common with other CT scanners. Still further, since the calculation for back projection is simple, the hardware is easy to build.

What is claimed is:

1. A CT scanner comprising:
  a scanning device including (a) means for rotating an x-ray source around an object to be examined, the x-ray source radiating x-rays, while the x-ray source is being rotated, in the form of fan beams covering a region of the object to be examined, and (b) a multi-element x-ray detector for detecting x-ray fan beams transmitted through the object to thus collect data during scanning of the x-ray source around the irradiated object;
  an arithmetic means for arithmetically reconstructing a distribution of x-ray absorption coefficients of the object across a measured cross-section from the data;
  a display means for displaying the distribution;
  where said arithmetic means includes a means for producing data equivalent to data derived from parallel beams not regularly spaced apart from each other from the collected data around the irradiated object, a means for subjecting the produced data to filtering, and a means for correcting the inhomogeneity in the data equivalent to data derived from parallel beams not regularly spaced and for back-projecting the image of the distribution; said means for producing data equivalent to data derived from parallel beams not regularly spaced establishes a two-dimensional coordinate space and performs arithmetic operations for rearrangement on a two-dimensional coordinate space which has first and second coordinate axes, the first coordinate axis corresponding to an angle that an x-ray beam detected by the multielement x-ray detector makes relative to an axis which is fixed relative to the object, the second coordinate axis being an inhomogeneous coordinate axis which is proportional to the inverse sine of a first quantity being between the center of rotation of the scanning device and the x-ray beam, and divided by a second quantity being the distance between the center of rotation and the x-ray source.

2. A CT scanner as set forth in claim 1, where the detecting elements of the multielement x-ray detector are regularly spaced from one another and said scanning device includes means for causing the x-ray source to radiate x-rays whenever the x-ray source rotates through a discrete step angle, the discrete step angle being equal to the product of (a) an integer times (b) the number of angular intervals between the regularly spaced, detecting elements of the multielement x-ray detector.

3. A CT scanner as set forth in claim 1 where said first quantity is equal to a distance measured along the normal from a line extending in the direction of the second distance.

* * * * *